(12) United States Patent
Cheng et al.

(10) Patent No.: US 7,635,471 B2
(45) Date of Patent: Dec. 22, 2009

(54) XYLANASE GENE SEQUENCES FROM THE GENOMIC DNA OF UNPURIFIED RUMEN MICROORGANISMS

(75) Inventors: Kou-Joan Cheng, Taipei (TW); Yo-Chia Chen, Pingtung (TW); Hsueh-Ling Cheng, Pingtung (TW); Shiou Hua Lin, Pingtung (TW); Je Ruei Liu, Taipei (TW); Bi Yu, Taichung (TW)

(73) Assignee: Genozyme Biotech Inc., Taipei (TW)

( * ) Notice: Subject to any disclaimer, the term of this patent is extended or adjusted under 35 U.S.C. 154(b) by 0 days.

(21) Appl. No.: 11/506,891

(22) Filed: Aug. 21, 2006

(65) Prior Publication Data

US 2008/0118491 A1     May 22, 2008

(51) Int. Cl.
*A61K 38/47* (2006.01)
*A61K 38/54* (2006.01)
*C12N 9/42* (2006.01)
*C12N 9/28* (2006.01)
*C12N 9/36* (2006.01)
*C07H 21/04* (2006.01)

(52) U.S. Cl. .................. 424/94.61; 424/94.2; 435/209; 435/202; 435/206; 435/183; 536/23.2; 536/23.7

(58) Field of Classification Search ........................ None
See application file for complete search history.

(56) References Cited

U.S. PATENT DOCUMENTS 5,612,055 A * 3/1997 Bedford et al. ............. 424/442
5,824,533 A * 10/1998 Li et al. ....................... 435/209

OTHER PUBLICATIONS

Whisstock et al., Prediction of protein function from protein sequence. Q. Rev. Biophysics., 2003, vol. 36 (3): 307-340.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Liu et al., Direct cloning of a xylanase gene from the mixed genomic DNA of rumen fungi and its expression in intestinal *Lactobacillus reuteri*. FEMS Microbiol Lett., 2005, vol. 251: 233-241.*
Bajpai, Critical Reviews in Biotechnology, vol. 24, No. 1, pp. 1-58 (2004).
Beg et al., Appl. Microbiol. Biotechnol., vol. 56, pp. 326-338 (2001).
Campbell et al., J. Nutr., vol. 127, pp. 137-145 (1997).
Henrissat et al., Biochem J., vol. 316, pp. 695-696 (1996).
Chen et al., FEMS Microbiology Letters, vol. 221, pp. 227-231 (2003).
Choct et al., British Poultry Science, vol. 33, pp. 821-834 (1992).
Cowieson et al., British Poultry Science, vol. 46, No. 6, pp. 717-724 (Dec. 2005).
Engberg et al., Poultry Science, vol. 83, pp. 925-938 (2004).
Henrissat et al., BJ Letters, pp. 350-351 (Apr. 3, 1995).
Howard et al., J. Nutr., vol. 125, pp. 2604-2609 (1995).
Huang et al., FEMS Microbiology Letters, vol. 243, pp. 455-460 (2005).
Lachke, Resonance, pp. 50-58 (May 2002).
Li et al., Applied and Environmental Microbiology, vol. 63, No. 2, pp. 628-635 (Feb. 1997).
Miller, Analytical Chemistry, vol. 31, No. 3, pp. 426-428 (Mar. 1959).
Saha, J. Ind Microbiol Biotechnol., vol. 30, pp. 279-291 (2003).
Teather et al., Applied and Environmental Microbiology, vol. 43, No. 4, pp. 777-780 (Apr. 1982).
Christov et al., Enzyme Microb. Technol., vol. 15, pp. 460-475 (1993).
Bruyer et al., Meded Rijksuniv Gent Fak Landbouwkd, Toegep Biol Wet., vol. 66, No. 3b, pp. 467-468 (2001) (abstract only).

* cited by examiner

*Primary Examiner*—Ganapathirama Raghu
(74) *Attorney, Agent, or Firm*—Birch, Stewart, Kolasch & Birch, LLP

(57) ABSTRACT

A xylanase gene, denoted xynR8, encoding a xylanase (XynR8) obtained from the unisolated rumen microorganisms is provided. The DNA sequence of the xynR8 gene, xylanase, is also provided, the enzyme is thermostable, and highly specific for xylans with high activity. Transformation of microbial hosts with the xynR8 gene is described. A method for degrading the xylan-containing structure comprises hydrolyzing the β-1,4-glycosidic bonds of xylans by contacting xylanase is provided, and a composition employing the above-mentioned hydrolyzing method is further addressed.

9 Claims, 9 Drawing Sheets

```
xynR8  actgttgctaaggcccaatggggtggaaacggtggtgcccctgctggtcaaaaattaagc  60
        T  V  A  K  A  Q  W  G  G  N  G  G  A  P  A  G  Q  K  L  S
xynR8  gtaggtggtggtcaaaaccaacataaaggtgttttcgatggcttcagttatgaaatctgg 120
        V  G  G  G  Q  N  Q  H  K  G  V  F  D  G  F  S  Y  E  I  W
xynR8  ttagataacaccggtggtagcggttccatgaccccttggtaaaggtgcaaccttcaaggct 180
        L  D  N  T  G  G  S  G  S  M  T  L  G  K  G  A  T  F  K  A
xynR8  gaatggagtgcagctgttaaccgtggtaacttccttgcccgtcgtggtcttgacttcggt 240
        E  W  S  A  A  V  N  R  G  N  F  L  A  R  R  G  L  D  F  G
xynR8  tctaccaaaaaggcaaccgattacgaatacatcggaatggattatgaagcaagttacaga 300
        S  T  K  K  A  T  D  Y  E  Y  I  G  M  D  Y  E  A  S  Y  R
xynR8  caaactgccagcgcaagtggtaactcccgtctctgtgtatacggctggttccaaaaccgc 360
        Q  T  A  S  A  S  G  N  S  R  L  C  V  Y  G  W  F  Q  N  R
xynR8  ggagttcaaggcgtacctttggtagaatactacatcattgaagattgggtcgactgggta 420
        G  V  Q  G  V  P  L  V  E  Y  Y  I  I  E  D  W  V  D  W  V
xynR8  ccagatgcacaaggaaaaaatggtaaccatcgatggtgcacaatataagattttccaaatg 480
        P  D  A  Q  G  K  M  V  T  I  D  G  A  Q  Y  K  I  F  Q  M
xynR8  gatcacactggtccaactatcaatggtggtaatgaaacctttaagcaatacttcagtgtc 540
        D  H  T  G  P  T  I  N  G  G  N  E  T  F  K  Q  Y  F  S  V
xynR8  cgtcaacaaaaagagaacttctggtcatatattactgtatcagatcactttaaggcatgggcc 600
        R  Q  Q  K  R  T  S  G  H  I  T  V  S  D  H  F  K  A  W  A
xynR8  agtcaaggttggggtattggaaaacctctatgaagttgcattgaacgcagaaggttggcaa 660
        S  Q  G  W  G  I  G  N  L  Y  E  V  A  L  N  A  E  G  W  Q
xynR8  agtagtggtgtcgctgacgtcaccaagttggatgtctacaccaccaaacaaggttctgct 720
        S  S  G  V  A  D  V  T  K  L  D  V  Y  T  T  K  Q  G  S  A
xynR8  cctcgtactaccaccaccactacccgtactactacccgtactactacaaaaacacttcca 780
        P  R  T  T  T  T  T  T  R  T  T  T  R  T  T  T  K  T  L  P
xynR8  accactggcaataagtgttctgccaagattactgcccaaggttacaagtgttgtagtgat 840
        T  T  G  N  K  C  S  A  K  I  T  A  Q  G  Y  K  C  C  S  D
xynR8  ccaaattgtgttatttactacactgatgacgatggtaaatgggg 884 (SEQ ID NO: 1)
        P  N  C  V  I  Y  Y  T  D  D  D  G  K  W  (SEQ ID NO: 2)
```

Fig. 3

```
xynR8       TVAKAQWGGNGGAPAGQKLSVGGGQNQHKGVFDGFSYEIWLDNTGGSGSMTLGKGATFKA 60
xynA_PC2    TVAKAQWGGNGGASAGQRLSVGGGQNQHKGVFDGFSYEIWLDNTGGSGSMTLGKGATFKA 60
xynw1-4NP   TVAKAQWGG--GASAGQKLSVGGGQNQHKGVSDGFSYEIWLDNTGGSGSMTLGSGATFKA 58
xynsk1-15NF TVAKAQWGG--GASAGQKLSVGGGQNQHKGVSDGFSYEIWLDNTGGSGSMTLGSGATFKA 58
            ******    *.********* **************** *** xynR8       EWSAAVNRGNFLARRGLDFGSTKKATDYEYIGMDYEASYRQTASASGNSRLCVYGWFQNR 120
xynA_PC2    EWSAAVNRGNFLARRGLDFGSTKKATAYEYIGLDYEASYRQTASASGNSRLCVYGWFQNR 120
xynw1-4NP   EWNAAVNRGNFLARRGLDFGSQKKATDYSYIGLDYTATYRQTASASGNSRLCVYGWFQNR 118
xynsk1-15NF EWNAAVNRGNFLARRGLDFGSQKKAADYSYIGLDYTATYRQTASASGNSRLCVYGWFQNR 118
             ************** *. * *. *.********************* xynR8       GVQGVPLVEYYIIEDWVDWVPDAQGKMVTIDGAQYKIFQMDHTGPTINGGNETFKQYFSV 180
xynA_PC2    GVQGVPLVEYYIIEDWVDWVPDAQGKMVTIDGAQYKIFQMDHTGPTINGGNETFKQYFSV 180
xynw1-4NP   GVQGVPLVEYYIIEDWVDWVPDAQGKMVTIDGAQYKIFQMDHTGPTINGGSETFKQYFSV 178
xynsk1-15NF GVQGVPLVEYYIIEDWVDWVPDAQGKMVTIDGAQYKIFQMDHTGPTINGGSETFKQYFSV 178
            ************************************************ ****** xynR8       RQQKRTSGHITVSDHFKAWASQGWGIGNLYEVALNAEGWQSSGVADVTKLDVYTTKQGSA 240
xynA_PC2    RQQKRTSGHITVSDHFKAWSNQGWGIGNLYEVALNAEGWQSSGVADVPKLDVYTTKQGSA 240
xynw1-4NP   RQQKRTSGHITVSDHFKEWAKQGWGIGNLYEVALNAEGWQSSGVADVTLLDVYTTPKGSS 238
xynsk1-15NF RQQKRTSGHITVSDHFKEWAKQGWGIGNLYEVALNAEGWQSSGVADVTLLDVYTTPKGSS 238
            ***************** *  *************************** ******  ** .

xynR8       PRTTTTTTRTTTRTTT--KTLPTTGNKCSAKITAQGYKCCSDPNCVIYYTDDDGKW 294 (SEQ ID NO: 1)
xynA_PC2    PRTTTTTTRTTTRTTT--KTLPTTNKKCSAKITAQGYKCCSDPNCVVYYTDEDGTW 294 (SEQ ID NO: 7)
xynw1-4NP   P-ATSAAPRTTTRTTTRTKSLPTNYNKCSARITAQGYKCCSDPNCVVYYTDDDGTW 293 (SEQ ID NO: 8)
xynsk1-15NF P-ATSAAPRTTTRTTTRTKSLPTNYNKCSARITAQGYKCCSDPNCVVYYTDDDGTW 293 (SEQ ID NO: 9)
            * -*... *******  *.*** .****.******************.****.** *
```

Fig. 4 ed States Patent

SEQUENCE LISTING

<160> NUMBER OF SEQ ID NOS: 9

<210> SEQ ID NO 1
<211> LENGTH: 884
<212> TYPE: DNA
<213> ORGANISM: Artificial Sequence
<220> FEATURE:
<223> OTHER INFORMATION: Artificially synthesized nucleotide

<400> SEQUENCE: 1

```
actgttgcta aggcccaatg gggtggaaac ggtggtgccc ctgctggtca aaaattaagc      60
gtaggtggtg gtcaaaacca acataaaggt gttttcgatg gcttcagtta tgaaatctgg     120
ttagataaca ccggtggtag cggttccatg acccttggta aaggtgcaac cttcaaggct     180
gaatggagtg cagctgttaa ccgtggtaac ttccttgccc gtcgtggtct tgacttcggt     240
tctaccaaaa aggcaaccga ttacgaatac atcggaatgg attatgaagc aagttacaga     300
caaactgcca gcgcaagtgg taactcccgt ctctgtgtat acggctggtt ccaaaaccgc     360
ggagttcaag gcgtaccttt ggtagaatac tacatcattg aagattgggt cgactgggta     420
ccagatgcac aaggaaaaat ggtaaccatc gatggtgcac aatataagat tttccaaatg     480
gatcacactg gtccaactat caatggtggt aatgaaacct ttaagcaata cttcagtgtc     540
cgtcaacaaa agagaacttc tggtcatatt actgtatcag atcactttaa ggcatgggcc     600
agtcaaggtt ggggtattgg aaacctctat gaagttgcat tgaacgcaga aggttggcaa     660
agtagtggtg tcgctgacgt caccaagttg gatgtctaca ccaccaaaca aggttctgct     720
cctcgtacta ccaccaccac tacccgtact actacccgta ctactacaaa aacacttcca     780
```

```
accactggca ataagtgttc tgccaagatt actgcccaag gttacaagtg ttgtagtgat      840
ccaaattgtg ttatttacta cactgatgac gatggtaaat gggg                      884
```

<210> SEQ ID NO 2
<211> LENGTH: 294
<212> TYPE: PRT
<213> ORGANISM: Artificial Sequence
<220> FEATURE:
<223> OTHER INFORMATION: Artificially synthesized peptide sequence

<400> SEQUENCE: 2

```
Thr Val Ala Lys Ala Gln Trp Gly Gly Asn Gly Gly Ala Pro Ala Gly
1               5                   10                  15

Gln Lys Leu Ser Val Gly Gly Gln Asn Gln His Lys Gly Val Phe
            20                  25                  30

Asp Gly Phe Ser Tyr Glu Ile Trp Leu Asp Asn Thr Gly Gly Ser Gly
        35                  40                  45

Ser Met Thr Leu Gly Lys Gly Ala Thr Phe Lys Ala Glu Trp Ser Ala
    50                  55                  60

Ala Val Asn Arg Gly Asn Phe Leu Ala Arg Arg Gly Leu Asp Phe Gly
65                  70                  75                  80

Ser Thr Lys Lys Ala Thr Asp Tyr Glu Tyr Ile Gly Met Asp Tyr Glu
                85                  90                  95

Ala Ser Tyr Arg Gln Thr Ala Ser Ala Ser Gly Asn Ser Arg Leu Cys
            100                 105                 110

Val Tyr Gly Trp Phe Gln Asn Arg Gly Val Gln Gly Val Pro Leu Val
        115                 120                 125

Glu Tyr Tyr Ile Ile Glu Asp Trp Val Asp Trp Val Pro Asp Ala Gln
    130                 135                 140

Gly Lys Met Val Thr Ile Asp Gly Ala Gln Tyr Lys Ile Phe Gln Met
145                 150                 155                 160

Asp His Thr Gly Pro Thr Ile Asn Gly Gly Asn Glu Thr Phe Lys Gln
                165                 170                 175

Tyr Phe Ser Val Arg Gln Gln Lys Arg Thr Ser Gly His Ile Thr Val
            180                 185                 190

Ser Asp His Phe Lys Ala Trp Ala Ser Gln Gly Trp Gly Ile Gly Asn
        195                 200                 205

Leu Tyr Glu Val Ala Leu Asn Ala Glu Gly Trp Gln Ser Ser Gly Val
    210                 215                 220

Ala Asp Val Thr Lys Leu Asp Val Tyr Thr Thr Lys Gln Gly Ser Ala
225                 230                 235                 240

Pro Arg Thr Thr Thr Thr Thr Arg Thr Thr Thr Arg Thr Thr
                245                 250                 255

Lys Thr Leu Pro Thr Thr Gly Asn Lys Cys Ser Ala Lys Ile Thr Ala
                260                 265                 270

Gln Gly Tyr Lys Cys Cys Ser Asp Pro Asn Cys Val Ile Tyr Tyr Thr
            275                 280                 285

Asp Asp Asp Gly Lys Trp
    290
```

<210> SEQ ID NO 3
<211> LENGTH: 20
<212> TYPE: DNA
<213> ORGANISM: Artificial Sequence
<220> FEATURE:
<223> OTHER INFORMATION: artificial synthesized primer sequence

```
<400> SEQUENCE: 3
actgttgcta aggcccaatg                                                    20

<210> SEQ ID NO 4
<211> LENGTH: 24
<212> TYPE: DNA
<213> ORGANISM: Artificial Sequence
<220> FEATURE:
<223> OTHER INFORMATION: artificial synthesized primer sequence

<400> SEQUENCE: 4
ccccatttac catcgtcatc agtg                                               24

<210> SEQ ID NO 5
<211> LENGTH: 33
<212> TYPE: DNA
<213> ORGANISM: Artificial Sequence
<220> FEATURE:
<223> OTHER INFORMATION: artificial synthesized primer sequence

<400> SEQUENCE: 5
cgggatcccg ttaactgttg ctaaggccca atg                                     33

<210> SEQ ID NO 6
<211> LENGTH: 34
<212> TYPE: DNA
<213> ORGANISM: Artificial Sequence
<220> FEATURE:
<223> OTHER INFORMATION: artificial synthesized primer sequence

<400> SEQUENCE: 6
atttgcggcc gctttacccc atttaccatc gtca                                    34

<210> SEQ ID NO 7
<211> LENGTH: 294
<212> TYPE: PRT
<213> ORGANISM: Orpinomyces sp.

<400> SEQUENCE: 7
```

Thr Val Ala Lys Ala Gln Trp Gly Gly Asn Gly Ala Ser Ala Gly
1               5                   10                  15

Gln Arg Leu Ser Val Gly Gly Gln Asn Gln His Lys Gly Val Phe
            20                  25                  30

Asp Gly Phe Ser Tyr Glu Ile Trp Leu Asp Asn Thr Gly Gly Ser
            35                  40                  45

Ser Met Thr Leu Gly Lys Gly Ala Thr Phe Lys Ala Glu Trp Ser Ala
    50                  55                  60

Ala Val Asn Arg Gly Asn Phe Leu Ala Arg Arg Gly Leu Asp Phe Gly
65                  70                  75                  80

Ser Thr Lys Lys Ala Thr Ala Tyr Glu Tyr Ile Gly Leu Asp Tyr Glu
                85                  90                  95

Ala Ser Tyr Arg Gln Thr Ala Ser Ala Ser Gly Asn Ser Arg Leu Cys
            100                 105                 110

Val Tyr Gly Trp Phe Gln Asn Arg Gly Val Gln Gly Val Pro Leu Val
        115                 120                 125

Glu Tyr Tyr Ile Ile Glu Asp Trp Val Asp Trp Val Pro Asp Ala Gln
    130                 135                 140

Gly Lys Met Val Thr Ile Asp Gly Ala Gln Tyr Lys Ile Phe Gln Met
145                 150                 155                 160

Asp His Thr Gly Pro Thr Ile Asn Gly Gly Asn Glu Thr Phe Lys Gln

```
                165                 170                 175
Tyr Phe Ser Val Arg Gln Gln Lys Arg Thr Ser Gly His Ile Thr Val
            180                 185                 190

Ser Asp His Phe Lys Ala Trp Ser Asn Gln Gly Trp Gly Ile Gly Asn
            195                 200                 205

Leu Tyr Glu Val Ala Leu Asn Ala Glu Gly Trp Gln Ser Ser Gly Val
            210                 215                 220

Ala Asp Val Pro Lys Leu Asp Val Tyr Thr Thr Lys Gln Gly Ser Ala
225                 230                 235                 240

Pro Arg Thr Thr Thr Thr Thr Arg Thr Thr Arg Thr Thr Thr
                245                 250                 255

Lys Thr Leu Pro Thr Thr Asn Lys Lys Cys Ser Ala Lys Ile Thr Ala
            260                 265                 270

Gln Gly Tyr Lys Cys Cys Ser Asp Pro Asn Cys Val Val Tyr Tyr Thr
            275                 280                 285

Asp Glu Asp Gly Thr Trp
        290

<210> SEQ ID NO 8
<211> LENGTH: 293
<212> TYPE: PRT
<213> ORGANISM: Neocallimastix patriciarum

<400> SEQUENCE: 8

Thr Val Ala Lys Ala Gln Trp Gly Gly Gly Ala Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
            35                  40                  45

Thr Leu Gly Ser Gly Ala Thr Phe Lys Ala Glu Trp Asn Ala Ala Val
        50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
        130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Val Ala Asp
        210                 215                 220

Val Thr Leu Leu Asp Val Tyr Thr Thr Pro Lys Gly Ser Ser Pro Ala
225                 230                 235                 240
```

Thr Ser Ala Ala Pro Arg Thr Thr Arg Thr Thr Arg Thr Lys
            245                 250                 255

Ser Leu Pro Thr Asn Tyr Asn Lys Cys Ser Ala Arg Ile Thr Ala Gln
            260                 265                 270

Gly Tyr Lys Cys Cys Ser Asp Pro Asn Cys Val Val Tyr Tyr Thr Asp
            275                 280                 285

Asp Asp Gly Thr Trp
    290

<210> SEQ ID NO 9
<211> LENGTH: 293
<212> TYPE: PRT
<213> ORGANISM: N. frontalis

<400> SEQUENCE: 9

Thr Val Ala Lys Ala Gln Trp Gly Gly Ala Ser Ala Gly Gln Lys
1               5                   10                  15

Leu Ser Val Gly Gly Gln Asn Gln His Lys Gly Val Ser Asp Gly
                20                  25                  30

Phe Ser Tyr Glu Ile Trp Leu Asp Asn Thr Gly Gly Ser Gly Ser Met
            35                  40                  45

Thr Leu Gly Ser Gly Ala Thr Phe Lys Ala Glu Trp Asn Ala Ala Val
50                  55                  60

Asn Arg Gly Asn Phe Leu Ala Arg Arg Gly Leu Asp Phe Gly Ser Gln
65                  70                  75                  80

Lys Lys Ala Ala Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
            115                 120                 125

Tyr Ile Ile Glu Asp Trp Val Asp Trp Val Pro Asp Ala Gln Gly Lys
            130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
            195                 200                 205

Glu Val Ala Leu Asn Ala Glu Gly Trp Gln Ser Ser Gly Val Ala Asp
            210                 215                 220

Val Thr Leu Leu Asp Val Tyr Thr Thr Pro Lys Gly Ser Ser Pro Ala
225                 230                 235                 240

Thr Ser Ala Ala Pro Arg Thr Thr Arg Thr Thr Arg Thr Lys
            245                 250                 255

Ser Leu Pro Thr Asn Tyr Asn Lys Cys Ser Ala Arg Ile Thr Ala Gln
            260                 265                 270

Gly Tyr Lys Cys Cys Ser Asp Pro Asn Cys Val Val Tyr Tyr Thr Asp
            275                 280                 285

Asp Asp Gly Thr Trp
    290

XYLANASE GENE SEQUENCES FROM THE GENOMIC DNA OF UNPURIFIED RUMEN MICROORGANISMS

FIELD OF THE INVENTION

The present invention relates to the fields of molecular biology and microbial biodiversity. In particular, the invention relates to a gene encoding xylanase obtained from unisolated strains of the rumen microorganisms. The xylanase can be used as an enzyme, which is thermostable and highly specific for xylans with high activity.

BACKGROUND OF THE INVENTION

Xylan is a major component of hemicellulose found predominantly in plant cell walls. Endo-xylanases (E.C. 3.2.1.8) are able to randomly hydrolyze the beta (1-4) glycosidic bonds between xylose residues making up the backbone of xylans. The xylanase enable plant structural polysaccharide to be hydrolyzed, and these products can be exploited as a rich source of carbon and energy for the growth of herbivores and microorganisms.

The plant cell wall consists largely of polysaccharides and contains lesser amounts of lignin and protein. The major polysaccharide components of plant cell walls are cellulose, hemicellulose, and pectin (Saha 2003). Fibrils of cellulose embedded in a matrix of pectin, hemicellulose (comprising various .beta.-xylan polymers), phenolic esters and protein produce a protective structure resistant to dehydration and penetration by phytopathogens through mechanical and enzymatic mechanisms. It represents a rich source of an important renewable resource utilized by the pulp and paper, lumber, food, and biofuel industries (Beg, Kapoor et al. 2001; Lachke 2002; Saha 2003; Bajpai 2004).

The plant structural polysaccharides provide an important protection for plant and useful applications for human, but these components also hinder men from much utilization of plant products. For example, cereals are a major component of diets fed to mono-gastric animals, the endosperm cell wall of cereals containing non-starch polysaccharide (NSP)(Engberg, Hedemann et al. 2004). The animals do not synthesize the enzymes capable of degrading these structural polysaccharides (e.g. hemicellulose), and as a result, these undigested NSP can often be problematic for mono-gastric animals being fed such a diet, causing intestinal disturbances, typified by sticky droppings and poor growth in young animals. It has been demonstrated previously that the anti-nutritive effects of NSP are related to their propensity to form high molecular-weight viscous aggregates in the gastrointestinal tract (Choct and Annison 1992). The problems and bad effects of hemicellulose also can be found in pulp making, pulp and juice production (Beg, Kapoor et al. 2001).

Hemicellulose, the second most prevalent polysaccharide in many plant cell walls is composed mainly of xyloglucan or xylan polymers. Xylans have a backbone structure of .beta. (1-4)-linked xylose residues. The structure of xylan is complicated by the attachment of various side chains (e.g., acetic acid, arabinose, coumaric acid, ferulic acid, glucuronic acid, 4-O-methylglucuronic acid) to the xylose residues (Saha 2003). The strands of hemicellulose are hydrogen bonded to cellulose fibrils to form a strong interconnected lattice. Cell wall composition varies with plant species, tissue type, growth conditions, and age.

Degradation of the plant cell wall is complicated by the structure of polysaccharides. Cellulose is a linear glucose polymer of β(1-4)-linkage and requires the synergistic hydrolysis of endoglucanase, and cellobiohydrolase and beta-glucosidase for complete degradation. In comparison, xylan is the most common in hemicellulosic polysaccharides. Xylan is a major polysaccharide comprising a backbone of xylose residues linked by β-1,4-glycosidic bonds. The main chain of xylan is composed of β-xylopyranose residues but highly substituted in its side chain, thus, xylan requires more and different enzymes, for complete degradation. An endoxylanase randomly cleaves the xylan backbone into xylooligosaccharides which are subsequently degraded to xylose by a xylosidase. Ferulic and p-coumaric acid crosslinks are degraded by feruloyl and p-coumaryl esterases. Substituents of xylan backbone are cleaved from the xylan backbone with arabinofuranidase, acetylxylan esterase and α-glucuronidase (Castanares 1992; Christov and Prior 1993; Saha 2003). Although various enzymes are necessary to the complete degradation, liquefaction of hemicellulose requires only the shortening of the xylan polymers. Consequently, this objective may be achieved by the production of xylooligosaccharides through the hydrolysis reaction of an endoxylanase (Beg, Kapoor et al. 2001).

Numerous applications of xylanases have been developed for many purposes. For instance, xylanases was used in biopulping to remove xylan impurities from cellulose pulps or to produce pulps with different characteristics. This green process is able to reduce the amount of chemical bleacher (chlorine) and the energy needed for refining pulp (Bajpai 2004). Xylanases can be the feeding enzyme, to improve the digestibility of cereal by poultry and swine fed on cereals with high arabinoxylan content (Beg, Kapoor et al. 2001; Bruyer, Giec et al. 2001; Cowieson, Hruby et al. 2005). Xylanases can be used in bioconversion involving the hydrolysis of xylan to xylooligosaccharides may not only serve as prebiotics for bifidobacteria (Howard, Gordon et al. 1995) but also provide an alternative and healthy sweetener for diabetics and portlies (Campbell, Fahey et al. 1997). Further, xylanases are useful in the retting of flax fibers, the clarification of fruit juices, the preparation of dextrans for use as food thickeners and the production of fluids and juices from plant materials (Beg, Kapoor et al. 2001).

Because of the important and potential applications of xylanases in industries, an important aspect of xylanase research is to obtain high activity and specification of xylanases. Consequently several bacteria and fungi have been selected for the sources of xylanase. Among xylanolytic microorganisms, rumen fungi are able to degrade the most-resistant plant cell-wall polymers, thus, the rumen fungal population represents a rich and underutilized source of novel enzymes with tremendous potential for industrial and agricultural applications. Those cellulases and xylanase produced by these fungi are among the most-active fibrolytic enzymes described to date, and many cellulase and xylanase genes have been cloned from specific strains such as *Orpinomyces* PC-2 (Li, Chen et al. 1997) and *Neocallimastix frontalis* SK (Huang, Huang et al. 2005). The recombinant products of the xylanase genes were presented highly active and specific activity of endoxylanase when expressed in *E. coli*.

In view of the foregoing, there remains a need for low cost xylanases having biochemical characteristics well suited for use in biobleaching, baking, animal feeding supplements, and xylooligosaccharide production. These previous xylanase genes usually obtained from the specific strain from rumen by molecular biology based specific technologies such PCR amplification, cDNA library construction and screening. Thus, the isolation of microbes from rumen would become one of the limitations to future successes at attempting to isolate novel genes and to comprehend the fibrolytic systems from rumen ecosystem. Accordingly, it is of great importance to obtain genes encoding xylan-degrading enzymes from novel sources. To the best of our knowledge, however, it is estimated that more than 90% of the total microbial population can not be isolated by currently known methods. In order to overcome such a problem and avoid complicated microbe-isolated protocols, the present invention provides a method directly obtain mixed genomic DNA from unpurified ruminal microbes as a gene source without isolating the microorganisms.

SUMMARY OF THE INVENTION

The fact has been proved that rumen is a rich source of microorganism which produce xylanases having biochemical characteristics desirable for industrial application such as animal feed supplementation and biobleaching. The rumen microorganism may be bacteria or fungi, as used herein, the rumen microorganisms particularly refer to the rumen fungi which have been identified as providing specific active xylanases capable of catalyzing the hydrolysis of backbone of xylose residues linked by β-1,4-glycosidic bonds. To make full use of the aforesaid characteristic in many ways, the primary object of the present invention is to provide an isolated and purified nucleic acid comprising a DNA sequence of SEQ ID NO:1 or a portion, a fragment, a variant or a complementary strand thereof.

Another object of the present invention is to provide an isolated and purified protein comprising an amino acid sequence of SEQ ID NO:2 or a portion, a fragment, or a variant thereof.

Yet another object of the present invention is to provide a host cell transformed with a DNA fragment comprising the DNA sequence of SEQ ID NO:1, which encodes a xylanase.

Yet another object of the present invention is to provide a method for isolating a xylanase gene from unisolated and mixed strains of rumen microorganisms and the method overcomes the obstacle in obtaining a xylanase gene from the mixed genomic DNA.

Yet another object of the present invention is to provide a method for degrading the β-1,4-glycosidic bonds of xylans by contacting the xylanase and the degrading products can be exploited as a rich source of carbon and energy for the growth of plants and microorganisms.

A further object of the present invention is to provide a composition for hydrolyzing the β-1,4-glycosidic bonds of xylans. The composition can be used as feed additives.

To achieve the aforesaid objects, the present invention provides an isolated and purified nucleic acid comprising a DNA sequence of SEQ ID NO:1; or a portion, a fragment, a variant or a complementary strand thereof.

Preferably, the nucleic acid is xylanse gene, and further, the DNA sequence of SEQ ID NO:1; or a portion, a fragment, a variant or a complementary strand thereof encoding a xylanase having an amino acid sequence of SEQ ID NO:2.

The present invention also provides an isolated and purified protein comprising an amino acid sequence of SEQ ID NO:2 or a portion, a fragment or a variant thereof.

Preferably, the amino acid sequence is SEQ ID NO:2, which is xylanase. The xylanse is an enzyme with thermostable and highly specific for xylans.

Furthermore, the present invention provides a host cell transformed with a DNA fragment encoding a xylanase, wherein the DNA fragment sequence is SEQ ID NO:1.

Preferably, the host cell is animal cell, plant cell, fungi cell, protozoan cell, prokaryotic host cell or virus. The xylanase encoded by the DNA fragment of SEQ ID. NO:1 comprises a amino acid sequence of SEQ ID NO:2.

Moreover, the present invention provides a method for isolating a xylanase gene from unisolated and mixed strains of rumen microorganisms which directly obtain mixed genomic DNA from unpurified ruminal microbes as a gene source without isolating or identifying the species of fungi, and the method can overcome the limitations of current known methods of isolating novel genes and to comprehend the fibrolytic systems from rumen ecosystem. It comprises the steps of: (a) obtaining rumen samples of unisolated and mixed strains of rumen microorganisms; (b) suspending said rumen samples in extraction buffer; (c) incubating said rumen samples and then adding proteinase K for incubating again; (d) extracting twice with phenol and twice with phenol-chloroform; (e) precipitating DNA with ethanol, and resuspending resulting DNA pellets in TE buffer to obtain extracted genomic DNA samples; (f) using said extracted genomic DNA samples as PCR template for amplification of DNA fragments; and (g) screening the xylanase gene from said amplified DNA fragments.

The present invention yet provides a method for degrading the xylan-containing structure, comprises hydrolyzing the β-1,4-glycosidic bonds of xylans by contacting the protein of an isolated and purified protein which comprises an amino acid sequence of SEQ ID NO:2 or a portion, a fragment or a variant thereof.

Preferably, the protein is xylanase with the characters of thermostable and highly specific for xylans.

Additionally, the present invention provides a composition for hydrolyzing the β-1,4-glycosidic bonds of xylans, comprising a xylanase containing SEQ ID NO: 2.

Preferably, the composition is used as food additives and the composition can further comprising proteases, alpha-amylase, cellulose, beta-glucanase or a mixture thereof.

To sum up, the present invention discloses a novel xylanase gene sequence, its encoded novel xylanase, and a method of hydrolyzing the β-1,4-glycosidic bonds of xylans disclosed herein are useful in numerous applications such as animal feed supplements, biobleacing or biofuel industries, etc. Hence, the present invention essentially provides the excellent way for implementation of green industry including cleaner production, resource recovery, and renewable energy.

BRIEF DESCRIPTION OF THE DRAWINGS

The above objects and advantages of the present invention will become more apparent with reference to the appended drawings wherein:

FIG. 3 exhibits nucleotide sequence (SEQ ID NO:1) and deduced amino acid sequence (SEQ ID NO:2) of xynR8 from mixed genoniic DNA of rumen fungi. The forward and reverse primers for PCR amplification are underlined. The putative region and conserved residues of glycol hydrolase family 11 are showed in bold type and double underline, respectively. The reiterated sequence RTTT is boxed.

FIG. 4 exhibits alignment of the deduced amino acid of xynR8 and xylanase genes of known rumen fungi. Amino acid residus with an identical match (*) and those with different degrees of conservation (: or .) are indicated. The reiterated sequences (RTTT) of linker are showed in bold type. Dockerin domains (partial) of xylanase are boxed. Gaps (dashes) were introduced to maximize the regions of sequence alignment. The reference sequences shown in this figure are *Orpinomyces* sp. PC-2 xylanase A (xynA, U57819)(SEQIDNO:7), *Neocallimastix patriciarum* W-1 xylanase W1-4(xynw1-4NP, AY133992)(SEQIDNO:8) and *N. frontalis* SK xylanase Sk1-15 (xynsk1-15, AY134032) (SEQIDNO:9).

DETAILED DESCRIPTION OF THE INVENTION

Figure 1:
FIG. 1 shows the mixed genomic DNA of rumen microorganisms. The genomic DNA of unisolated microorganisms was extracted by phenol-chloroform methods, separated on an agarose gel and visualized after ethidium bromide staining.

The present invention is described as follows. The diagrams accompanying the descriptions below are not presented in actual proportion; they are used only for illustration of the equipment setup of the present invention.

The present invention relates to a method for isolating a xylanase gene, denoted xynR8, from unisolated and mixed strains of rumen microorganisms, comprising the steps of: (a) obtaining rumen samples of unisolated and mixed strains of rumen icroorganisms; (b) suspending said rumen samples in extraction buffer; (c) incubating said rumen samples and then adding proteinase K for incubating again; (d) extracting twice with phenol and twice with phenol-chloroform; (e) precipitating DNA with ethanol, and resuspending the resulting DNA pellet in TE buffer to obtain extracted genomic DNA samples; (f) using said extracted genomic DNA samples as PCR template for amplification of DNA fragments; and (g) screening the xylanase gene from said amplified DNA fragments.

The aforesaid method of isolating the xynR8 gene encoding a xylanase which features the use of the mixed genomic DNA without isolating and identifying process, and it obtains a novel gene fragment showing about 20% divergence in DNA sequence from ones using of prior arts in the same field. Besides, it expresses outstandingly high enzyme activity in *E. coli* (Table 1, as below example 7).

Furthermore, xynR8 gene encoding a xylanase of the present invention operably is linked to control sequences capable of directing expression of the xylanase in a suitable host cell. As used herein "host cell" includes animal, plant, fungi, protozoan, prokaryotic host cells and virus. For example, the host cell, which includes eubacteria and archaebacteria, can be transformed with a DNA encoding a xylanase of the present invention so that the gene modified prokaryotes is capable of expressing the xylanase. The fungi can follow the same protocol and express the xylanase, as used herein, "fungi" includes filamentous and yeast form fungi.

In another preferred embodiment of the present invention, the method for degrading the xylan-containing structure, comprises hydrolyzing the β-1,4-glycosidic bonds of xylans by contacting the protein comprising an amino acid sequence of SEQ ID NO:2 or a portion, a fragment or a variant thereof. The hydrolyzing enzyme is namely xylanase which degrading the β-1,4-glycosidic bonds between xylose residues making up the backbone of xylans being a major plant structure polysaccharides. Additionally, hemicellulose, the second most prevalent polysaccharide in plant cell wall, is also hydrolyzed by the same mechanism. And then, it can promote the development of relative applications of xylanase in industry, such as pulp making, lumber, food and biofuel.

Accordingly, the invention extends to novel feed compositions and feed additives containing a xylanase of the present invention. Such feed compositions and supplements may also contain other enzymes, such as, proteases, alpha-amylase, cellulase, and beta-glucanase. The xylanase may be added directly to an untreated, pelletized, or otherwise processed feedstuff or it may be provided separately from the feedstuff in, for instance, powder, a pill, a gel formulation, a liquid formulation, or in drinking water. The invention extends to feed inoculant preparations comprising lyophilized microorganisms which express xylanases of the present invention under normal growing conditions. With respect to these feed inoculant preparations, "normal growing conditions" mean culture conditions prior to harvesting and lyophilization of the microorganisms. The microorganisms express xylanases during growth of the microbial cultures in large-scale fermenters. The activity of xylanase in the microorganisms is preserved by lyophilization of the harvested microbial concentrates containing the xylanase.

In conclusion, xylanases of the present invention are useful in a wide variety of applications involving the hydrolysis of xylan. Such applications include use in animal feed supplements, biobleaching and xylooligosaccharide production. Xylanases of the present invention may also be used to convert the hemicellulose of plant to biofuels (i.e., alcohol). The xylan content of certain feedstuffs such as cerels decreases their value as protein sources for fish, monogastric animals, young ruminants and infants because the xylan decreases the bioavailability of nutrients by circumventing structural polysaccharides, and limiting amino acids and proteins. Treatment of such feedstuffs with the xylanase of the present invention will reduce their xylan content by xylanase mediated hydrolysis, rendering the feedstuffs more suitable for use as protein sources and providing xylooligosaccharides for intestinal probiotics. It is to be understood that the following examples of the present invention should not be based to restrict the invention, and that all equivalent modifications and variations made without departing from the intent and import of the following descriptions of the examples should be included in the following claims.

EXAMPLES

Example 1

Rumen Sample Preparation and DNA Extraction

Rumen content from a water buffalo was sampled through a cannula, fragmented by a blender and squeezed through 2 layers of cheesecloth, following which 0.5 ml of filtrate was syringed into a Hungate tube (125×16 mm, Bellco Glass) containing 5 ml enrichment medium. For the suppression of bacterial growth, 1.2% (w/v) penicillin-G, 0.265% (w/v) streptomycin and 0.06% (w/v) chloramphenicol were used. The enrichment method as reported by Chen et al. was followed throughout (Chen, Hseu et al. 2003). The tubes containing medium and rumen fluid were incubated at 39° C. for 1 day, and the biomass was collected by centrifuge (4° C., 6000 rpm, 30 min). All of the samples used for DNA extraction had been frozen in liquid nitrogen, ground to a fine powder with a mortar and pestle, and then stored at −20° C.

The protocols for DNA extraction was based upon phenol-chloroform extraction. Rumen samples were resuspended in extraction buffer (25 mM Tris-HCl, pH 8.0; 10 mM EDTA; 50 mM glucose; 0.5% (w/v) Sodium dodecyl sulfate (SDS)) and incubated at 37° C. for 1 h. Proteinase K (0.1 mg/mL) was added, and the mixture was incubated for 1 h at 55° C., extracted twice with phenol and twice with phenol-chloroform. The DNA was precipitated with ethanol, and the resulting DNA pellet resuspended in TE (10 mM Tris, pH 8.0; 1 mM EDTA) buffer. The extracted genomic DNA samples were examined by agarose electrophoresis (FIG. 1) and stored at −20° C. prior to use.

Example 2

Amplification of the Xylanase Gene from Rumen Microbial Genomic DNA

Figure 2:
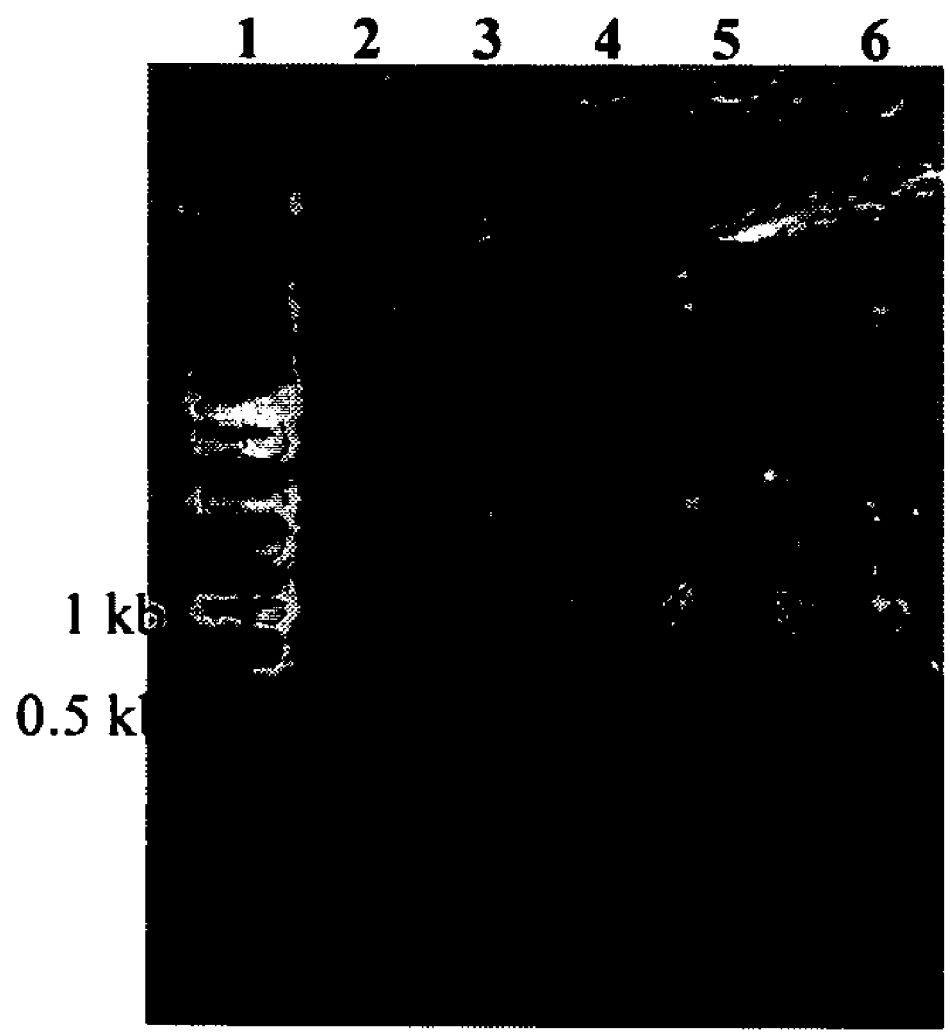
FIG. 2 shows PCR results of the xylanase gene amplification. Lane 1, DNA marker (1 kb ladder). Lane 2-4, first PCR products amplified by using xynF4 and xynR2 primers. Lane 5-6, secondly amplified PCR fragments extended from BamHI-xynF4 and NotI-xynR2 primers.

The PCR reaction adopted herein was used for the amplification of xylanase genes obtained from the mixed genomic DNA samples extracted from unpurified rumen microorganism cultures. Two primers, xynF4 (5'-ACTGTTGCTAAG-GCCCAATG-3')(SEQ ID NO:3) and xynR2 (5'-CCCCATT-TACCATCGTCATCAGTG-3')(SEQ ID NO:4), were designed based upon the rumen fungal xylanase sequences. The reaction conditions of PCR are as follows: under 94.degree. C. for 2 minutes, and then successively repeating the following four conditions for 35 times: (1) under 94.degree. C. for 45 seconds (denature DNA), (2) under 45.degree. C. for 45 seconds, (3) under 72.degree. C. for 90 seconds, (4) under 72.degree. C. for 10 minutes. The amplified products were examined by agarose gel electrophoresis (FIG. 2). The diluted PCR product so produced was subsequently amplified again using BamHI-xynF4 (5'-CGG-GATCCCGTTAACTGTTGCTAAGGCCCAATG-3')(SEQ ID NO:5) and NotI-xynR2 primers (5'-ATTTGCGGC-CGCTTTACCCCATTTACCATCGTCA-3') (SEQ ID NO:6) and an appropriate PCR process. BamHI and NotI restriction sites were incorporated into xynF4 and xynR2, respectively, in order to facilitate the cloning of the xylanase gene to the pGEX4T-1 (Amersham-Pharmacia, Piscatway, N.J.) expression vector for subsequent screening purposes. The reaction conditions of secondary PCR are as follows: under 94.degree. C. for 1 minutes, and then successively repeating the following four conditions for 35 times: (1) under 94.degree. C. for 30 seconds (denature DNA), (2) under 52.degree. C. for 45 seconds, (3) under 72.degree. C. for 90 seconds, (4) under 72.degree. C. for 10 minutes. The PCR fragments were also analyzed on an agarose gel (FIG. 2).

Example 3

Screening of the Xylanase Gene from Amplified DNA Fragments

The xylanase gene enriched pool was constructed by ligating the BamHI- and NotI-digested (New England Biolabs, Beverly, Mass.) PCR products into the pGEX4T-1 vector. The ligation mixture was used to transform *E. coli* DH5α (Invitrogen, Carlsbad, Calif.) by electroporation (Sambrook and Russell 2001). The electroporated cells were spread on Luria-Bertani (LB) agar (Difco, Detroit, Mich.) containing 0.2% xylan (Oat spelt, Sigma, St. Louis, Mo.). Subsequent to overnight incubation at 37 degree. C, the transformants were transferred to another LB plates and screened by Congo-red staining (Teather and Wood 1982). Those colonies surrounded by clear zone indicated a level of xylanase activity of the clones. The resultant plasmids (pGEX4T-1R8) were purified and the sequence of the xylanase gene (xynR8) inserts was determined by automatic sequencing (MDBio Inc. Taipei). The nucleotide sequence of xynR8 has been deposited with GenBank (Accession No. AY941119).

Example 4

Nucleotide Sequence and Structural Analyses of the xynR8 Gene

The computer program Bioedit was used to analyze and align the xylanase sequences. Sequence analysis of the inserts in the plasmids obtained from the clones revealed that pGEX4T-1R8 contained The total length of the xylanase insert (xynR8) was 884 bp (FIG. 3). The deduced amino acid sequence of xynR8 was significantly similar to those of several anaerobic fungal xylanases belonging to family 11 glycosyl hydrolases (FIG. 4)(Henrissat and Romeu 1995; Henrissat and Bairoch 1996). xynR8 exhibited an amino acid sequence highly similar to that of xynA of *Orpinomyces* sp. PC-2 (Accession No. U57819), xynw1-4 of *N. patriciarum* (Accession No. AY133992) and xynsk1-15 of *N. frontalis* (Accession No. AY134032). The xynR8 gene revealed amino acid identities of 95.9%, 89.1% and 88.8% when compared, respectively, with xynA, xynw1-4 and xynsk1-15.

Example 5

Overexpression of the Rumen Microbial Xylanase Gene (xynR8)

Isolation and characterization of xynR8 from uncultured rumen microbes enables the large scale production of Xylanase R8 in any of a number of prokaryotic (e.g., *E. coli*, lactic acid bacteria and *B. subtilis*) or eukaryotic (e.g., fungal— *Pichia, Saccharomyces, Aspergillus, Trichoderma*; plant— *Brassica, Zea, Solanum*; or animal—poultry, swine or fish) expression systems using known methods.

Example 6

Cloning of the xynR8 in an *Escherichia coli*-Specific Expression Construct To obtain abundant xylanase, the xynR8 was fused with T7 promoter for efficient expression in *E. coli*. A number of *E. coli* expression vectors based on the T7 promoters are commercially available. The xylanase gene (xynR8) was subcloned into pET21a (Novagen Inc.) and generated pET21aR8. Strain suitable for high levels of protein expression, such as BL21 (DE3), is employed. Positive clones are further characterized by nucleotide sequence analysis. The resultant plasmids were transformed into E. coli BL21 (DE3) to express recombinant proteins. All recombinant proteins had the His6-tag at each protein C-termini.

Example 7

The Expression and Purification of Recombinant XYNR8

For the xylanase production in E. coli, the positive clone was grown in 500 ml LB to an OD600 of 0.6-0.9 before 0.5 mM of IPTG (isopropyl-thio-β-D-galactopyranoside) was added for the induction. After 3.5 h of induction at 37. degree C., the cells were harvested by centrifugation (4000 g, 10 min) for recombinant protein purification.

The expressed XynR8 can be extracted by sonication the E. coli cells. Protein inclusions of XynR8 can be harvested by centrifugation. The xylanase activity of prepared cell extracts was assayed by DNS methods, One unit of xylanase activity was defined as one μmol of reducing sugar equivalents released per minute.

Figure 5:
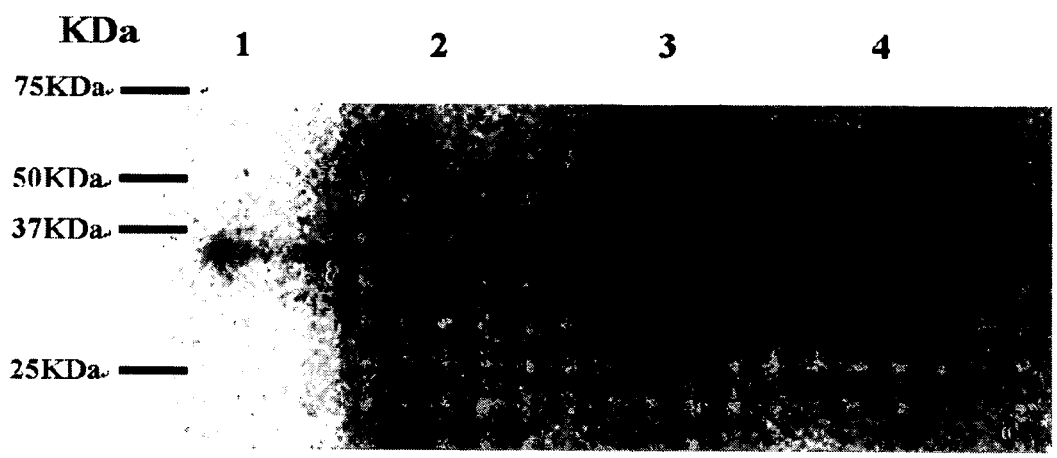
FIG. 5 shows Western blotting using anti-His tag antibody. The IPTG-induced *E. coli* BL21 (DE3) broth and cells were divided into 4 fractions. Each fraction was detected by Western blotting using the monoclonal anti-His tag antibody. Lane 1, extracellular broth. Lane 2, Periplasmic space. Lane 3, cytoplasm extract. Lane 4, insoluble precipitate.
Figure 6:
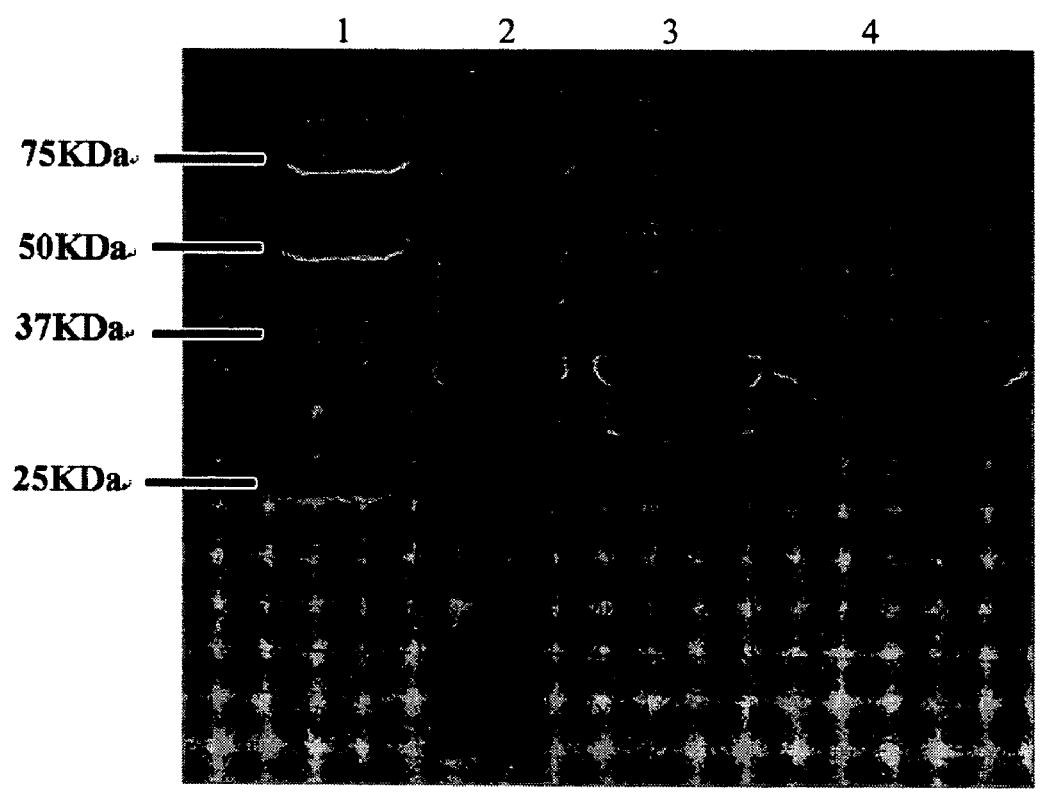
FIG. 6 shows SDS-PAGE analysis of XYNR8. The intercellular extract of pET21aR8 transformed *E. coli* was purified by CM and Ni-NTA chromatography. Lane 1, protein standard. Lane 2, intercellular extract. Lane 3, CM-column purified products. Lane 4. Ni-NTA column purified XYNR8

Fusion protein purification was performed using ion-exchange (CM-shepharose, Amersham Bioscience) and nickel affinity (Ni-NTA-agarose, Qiagen) columns. The recombinant protein was dialyzed with citrate buffer (50 mM, pH6) to remove imidazol. Protein concentrations were determined using a Micro BCA Protein Assay Reagent Kit (Pierce Biotechnology, Rockford, Ill.). FIG. 6 and table 1 illustrate show the results of purification steps, and a 34 KDa product was obtained after a Ni-NTA affinity chromatography. The product was also confirmed by Western blotting (FIG. 5). Table 2 summarizes the purification steps of XYNR8. XYNR8 had the highest specific activity (23244.85 U/mg) against oat spelt xylan.

Example 8

Biochemical Characteristics of the XYNR8

Figure 7:
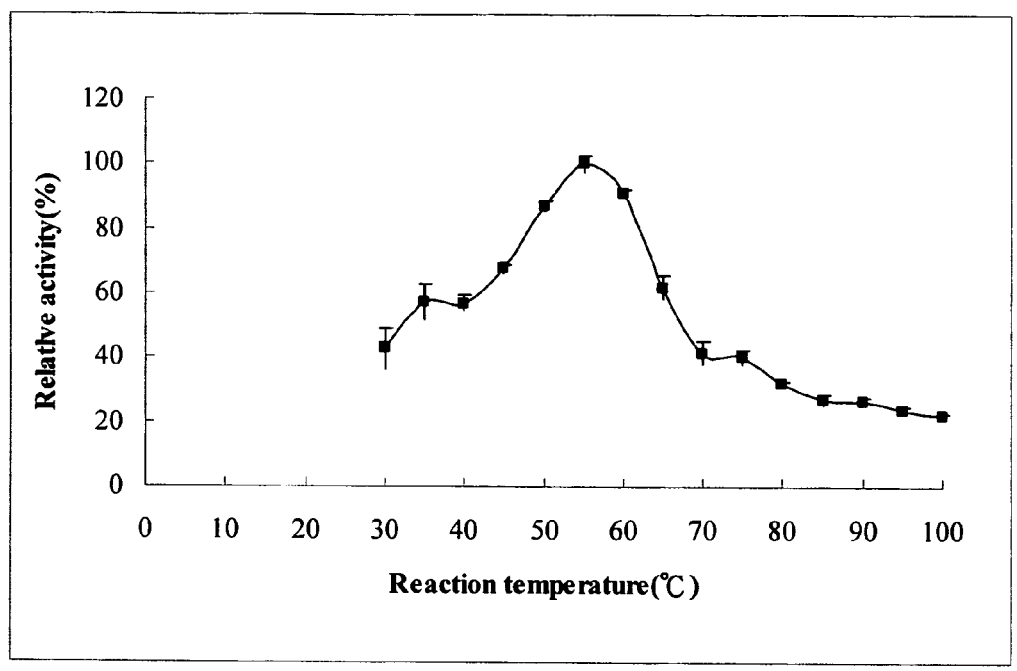
FIG. 7 illustrates the temperature optima for xylanase (XYNR8) activities. The optimal reaction temperature is 50 degree C.
Figure 8:
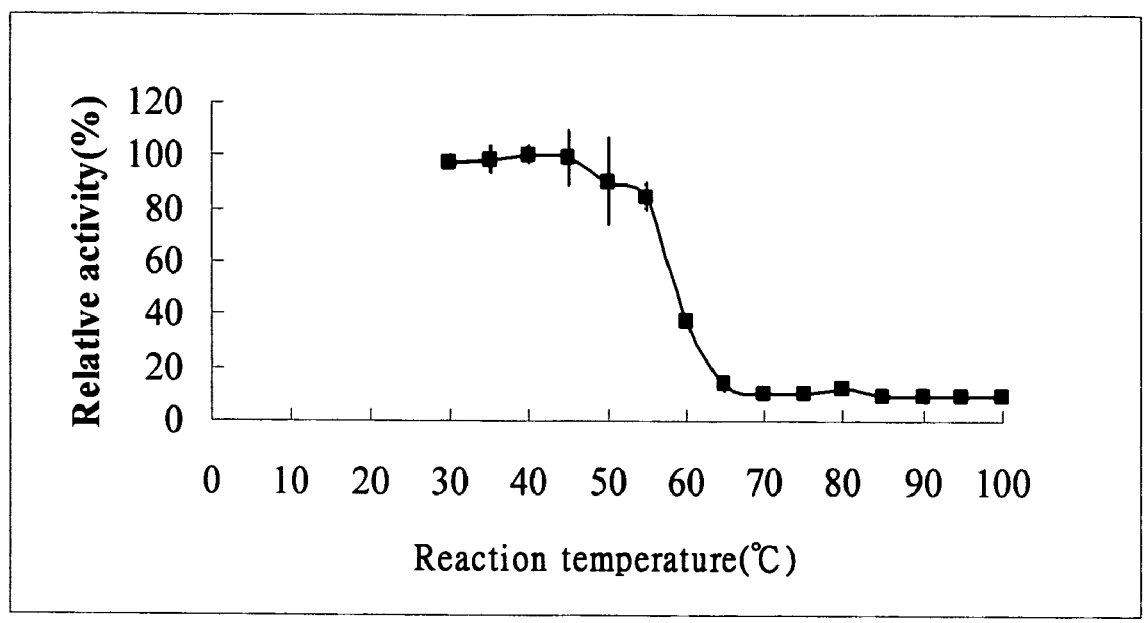
FIG. 8 illustrates the thermostability of XYNR8. XYNR8 showed a broad range of thermostability when hydrolyzed oat spelt xylan.

The biochemical characteristics of the recombinant xylanase were determined using purified xylanase. Xylanase activity was determined by measuring the amount of reducing sugars released from substrates according to the method of DNS method (Miller 1959). The temperature optimum for the purified xylanase activity was 55.degree. C. (FIG. 7), and the enzyme was thermostable when treated in 30-55.degree. C. for 10 minutes (FIG. 8). These suggest that the enzyme is able to acclimatize various applications of industries. The $V_{max}$ and $K_m$ for oat spelt xylan hydrolysis were 1.1 mM/min and 11.1 mg/ml, respectively, and the value of $K_{cat}$ for oat spelt xylan hydrolysis was 38943.2 $sec^{-1}$. The XYNR8 showed high specific to the xylan substrates as the above-mentioned table 2. XYNR8 hydrolyzed oat spelt xylan, birchwood xylan and birch wood xylan well, and it gave the highest specific activity against soluble xylan.

XYNR8 against different polysaccharide substrates were also examined. The enzyme were inactive against starch, cellulobiose, CMC (carboxylmethyl cellulose) and avicel.

Example 9

Xylan Hydrolysis by the Recombinant Xylanase XynR8

Figure 9:
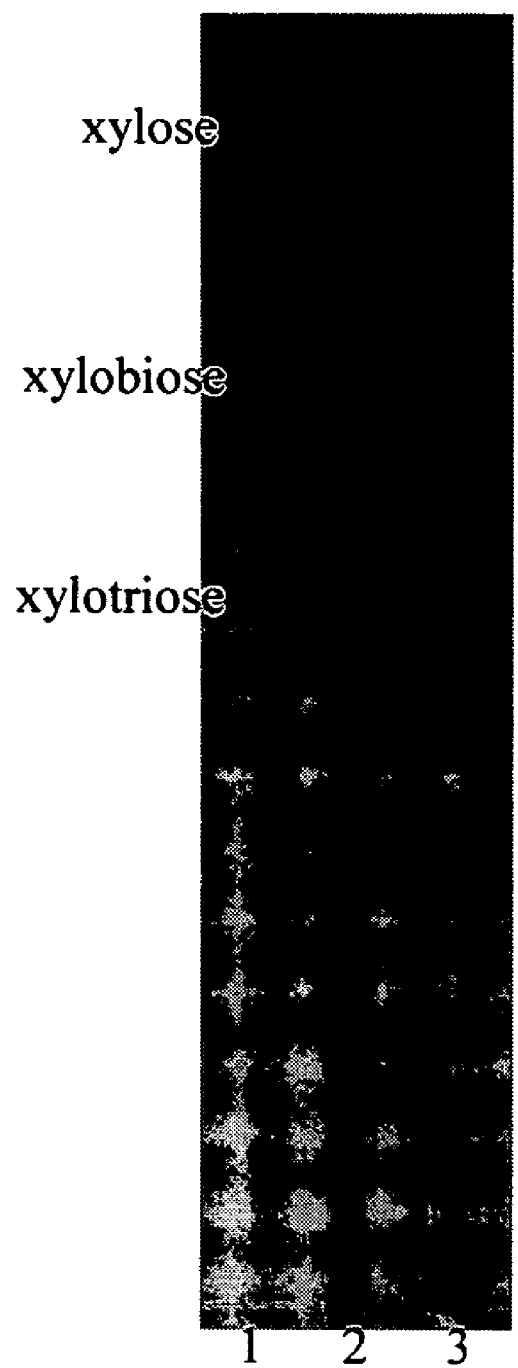
FIG. 9 shows TLC analysis of the hydrolysis products released from oat spelt xylan by xylanase from *E. coli* BL21 (DE3). Lane 1, Xylooligosaccharide standard. Lane 2, the hydrolysis products of xylan.

The hydrolysis products released from oat spelt xylan by XynR8 were analyzed using TLC (Thin layer chromatography), the results being presented in FIG. 9. The principal products of xylan hydrolysis of oat spelt xylan were xylobiose and xylotriose, which indicated that the recombinant xylanase was an endoxylanase, and the pattern of such hydrolysis classified the xylanase R8 as being endoenzyme b-1,4 xylan xylanohydrolase (EC 3.2.1.8)(Huang, Huang et al. 2005) This result also suggests XYNR8 has the ability to hydrolyze the xylan of hemicellulose.

Other Embodiments

It is to be understood that the foregoing description of the present invention should not be based to restrict the invention, and that all equivalent modifications and variations made without departing from the intent and import of the foregoing description should be included in the following claim.

REFERENCES

Bajpai, P. (2004). "Biological bleaching of chemical pulps." Crit Rev Biotechnol 24(1): 1-58.
Beg, Q. K., M. Kapoor, et al. (2001). "Microbial xylanases and their industrial applications: a review." Appl Microbiol Biotechnol 56(3-4): 326-38.

TABLE 1

Purification of XYN from xynR8 transformed E. coli.

| Purification step | Volume (mL) | Total Activity (U) | Protein (mg) | Specific activity (U/mg) | Purification Fold | Recovery (%) |
|---|---|---|---|---|---|---|
| Crude extract | 22.5 | 108037.74 | 42.07 | 2568.27 | 1 | 100 |
| CM-Sepharose column | 9.5 | 76639.69 | 5.26 | 14568.65 | 5.7 | 71 |
| Ni-NTA column | 9.5 | 75510.80 | 3.25 | 23244.85 | 9.1 | 70 |

TABLE 2

Substrate specificity of XYNR8

| Substrate(2%) | Relative activity(%) |
|---|---|
| Oat spelt xylan | 27.36 |
| Soluble oat spelt xylan | 100 |
| Birchwood xylan | 67.18 |
| Beechwood xylan | 38.80 |
| Xylooligosaccharides(X2, X3) | 1.83 |
| Cellulose | 0 |
| Avicel | 0 |
| Carbonxymethyl cellulose | 0 |
| Starch | 0 |
| Cellobiose | 0 |

Bruyer, D., R. Giec, et al. (2001). "Effect of a bacterial xylanase and/or antibiotic growth promoter on zootechnical performances of piglets fed arabinoxylan rich diets." *Meded Rijksuniv Gent Fak Landbouwkd Toegep Biol Wet* 66(3b): 467-8.

Campbell, J. M., G. C. Fahey, Jr., et al. (1997). "Selected indigestible oligosaccharides affect large bowel mass, cecal and fecal short-chain fatty acids, pH and microflora in rats." *J Nutr* 127(1): 130-6.

Castanares, A. (1992). "Hemicellulose and Hemicellulases, M. P. Coughlan and G. Hazelwood, Eds." *Portland Press, Cambridge, U.K.:* 85-102.

Chen, Y. C., R. S. Hseu, et al. (2003). "The genetic similarity of different generations of *Neocallimastix frontalis* SK." *FEMS Microbiol Lett* 221(2): 227-31.

Choct, M. and G. Annison (1992). "Anti-nutritive effect of wheat pentosans in broiler chickens: roles of viscosity and gut microflora." *Br. Poult. Sci.* 33(821?34).

Christov, L. P. and B. A. Prior (1993). "Esterases of xylan-degrading microorganisms: production, properties, and significance." *Enzyme Microb Technol* 15(6): 460-75.

Cowieson, A. J., M. Hruby, et al. (2005). "The effect of conditioning temperature and exogenous xylanase addition on the viscosity of wheat-based diets and the performance of broiler chickens." *Br Poult Sci* 46(6): 717-24.

Engberg, R. M., M. S. Hedemann, et al. (2004). "Influence of whole wheat and xylanase on broiler performance and microbial composition and activity in the digestive tract." *Poult Sci* 83(6): 925-38.

Henrissat, B. and A. Bairoch (1996). "Updating the sequence-based classification of glycosyl hydrolases." *Biochem J* 316 (Pt 2): 695-6.

Henrissat, B. and A. Romeu (1995). "Families, superfamilies and subfamilies of glycosyl hydrolases." *Biochem J* 311 (Pt 1): 350-1.

Howard, M. D., D. T. Gordon, et al. (1995). "Dietary fructooligosaccharide, xylooligosaccharide and gum arabic have variable effects on cecal and colonic microbiota and epithelial cell proliferation in mice and rats." *J Nutr* 125(10): 2604-9.

Huang, Y. H., C. T. Huang, et al. (2005). "Effects of dockerin domains on *Neocallimastix frontalis* xylanases." *FEMS Microbiol Lett* 243(2): 455-60.

Lachke, A. (2002). "Biofuel from D-xylose—the Second Most Abundant Sugar." *Resonance* (50-58).

Li, X. L., H. Chen, et al. (1997). "Monocentric and polycentric anaerobic fungi produce structurally related cellulases and xylanases." *Appl Environ Microbiol* 63(2): 628-35.

Miller, G. L. (1959). "Use of dinitrosalicylic acid reagent for determination of reducing sugar." *Anal Chem* 31(426-428).

Saha, B. C. (2003). "Hemicellulose bioconversion." *J Ind Microbiol Biotechnol* 30(5): 279-91.

Sambrook, J. and D. W. Russell (2001). "Molecular cloning: a laboratory manual." 3rd ed. *Cold Spring Harbor Laboratory Press, Cold Spring Harbor, N.Y.*

Teather, R. M. and P. J. Wood (1982). "Use of Congo red-polysaccharide interactions in enumeration and characterization of cellulolytic bacteria from the bovine rumen." *Appl Environ Microbiol* 43(4): 777-80.

---

What is claimed is:

1. An isolated and purified protein, comprising the amino acid sequence of SEQ ID NO:2.

2. The protein of claim 1, wherein said amino acid sequence is SEQ ID NO: 2.

3. The protein of claim 1, which is a xylanase.

4. The protein of claim 3, wherein said xylanase is a thermostable enzyme and specific for xylans.

5. A composition for hydrolyzing the β-1,4-glycosidic bonds of xylans, comprising a xylanase containing SEQ ID NO: 2.

6. The composition of claim 5, which further comprises proteases, alpha-amylase, cellulase, beta-glucanase or a mixture thereof.

7. A method for degrading xylans in a xylan-containing structure, wherein said method comprises hydrolyzing the β-1,4-glycosidic bonds of xylans by contacting with the protein of claim 1.

8. The method of claim 7, wherein said protein contains SEQ ID NO: 2.

9. The method of claim 8, wherein said protein is xylanase.

* * * * *